United States Patent
Eliu et al.

(10) Patent No.: US 7,785,375 B2
(45) Date of Patent: Aug. 31, 2010

(54) PYRIDO THIAZINIUM DYES

(75) Inventors: Victor Paul Eliu, Lörrach (DE); Beate Fröhling, Grenzach-Wyhlen (DE); Dominique Kauffmann, Illzach (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/922,660

(22) PCT Filed: Jun. 21, 2006

(86) PCT No.: PCT/EP2006/063374

§ 371 (c)(1),
(2), (4) Date: Mar. 4, 2009

(87) PCT Pub. No.: WO2007/003506

PCT Pub. Date: Jan. 11, 2007

(65) Prior Publication Data

US 2009/0300855 A1    Dec. 10, 2009

(30) Foreign Application Priority Data

Jul. 1, 2005  (EP) .................... 05105997

(51) Int. Cl.
*A61Q 5/10* (2006.01)
*C07D 279/00* (2006.01)

(52) U.S. Cl. .............. 8/405; 8/425; 8/565; 8/575; 8/587; 544/47; 132/202; 132/208

(58) Field of Classification Search .......... 8/405, 8/425, 565, 575, 587; 544/47; 132/202, 132/208

See application file for complete search history.

(56) References Cited

U.S. PATENT DOCUMENTS 3,100,739 A * 8/1963 Berth et al. .......... 8/426

FOREIGN PATENT DOCUMENTS

GB    2056475    3/1981

WO    95/01772    1/1995

OTHER PUBLICATIONS

STIC Search Report dated Jan. 29, 2010.*

* cited by examiner

*Primary Examiner*—Eisa B Elhilo
(74) *Attorney, Agent, or Firm*—Tyler A. Stevenson

(57) ABSTRACT

Disclosed is a method of dyeing keratin-containing fibers comprising treating the fiber with at least one compound of formula (1), wherein $R_1, R_2, R_3, R_4$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-C5alkyl; —$NR_5R_6$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; $R_5$ and $R_6$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C1$-$C_5$alkyl, $C_1$-$C_5$alkoxy, halogen, —$NH2$, mono-$C_1$-$C_5$alkylamino, di-$C_1$-C5alkylamino, —$NO_2$, carboxy or hydroxy; and An is an anion. Furthermore, the present invention relates to novel heterocyclic compounds, compositions thereof, especially comprising other dyes, and to processes for their preparation and application to hair dying.

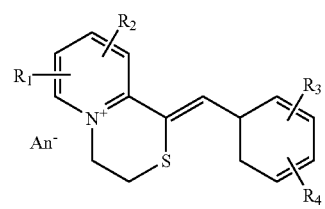

(I)

12 Claims, No Drawings

PYRIDO THIAZINIUM DYES

The present invention relates to novel heterocyclic compounds, compositions thereof, to processes for their preparation and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

R. S. Asquith, P. Carthew and T. T. Francis describe in JSDC from May 1973, pages 168-172 that ortho-azo disulfide dyes do not lead to covalent bonding with keartin fiber of wool, and that para-azo disulfide dyes underwent only at high concentration some covalent bindings with wool.

The technical problem is to provide dyes that are distinguished by deep dyeing having good fastness properties with respect to washing, light, shampooing and rubbing.

Accordingly, the present invention relates to a method of dyeing keratin-containing fibers, comprising treating the fiber with at least one compound of formula

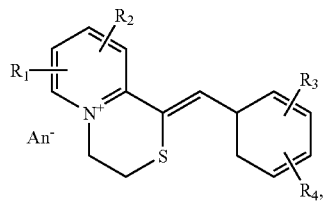

(1)

wherein $R_1$, $R_2$, $R_3$, $R_4$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_5R_6$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_5R_6$;

$R_5$ and $R_6$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy; and An is an anion.

Compounds of formula (1) are preferably used, wherein $R_1$ is identical to $R_2$.

Preferably in formula (1)

$R_1$, $R_2$ and $R_3$ independently from each other are hydrogen; or $C_1$-$C_{12}$alkyl; and $R_4$ is defined as in formula (1).

Preferably in formula (1)

$R_4$ is hydrogen; $C_1$-$C_5$-alkoxy; halogen; or —$NR_5R_6$, wherein $R_5$ and $R_6$, independently from each other are hydrogen; $C_1$-$C_{12}$alkyl; —(CO)—H; or —(CO)—$C_1$-$C_5$alkyl.

Most preferred heterocyclic compounds correspond to formula

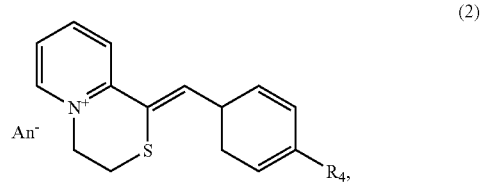

(2)

wherein $R_4$ is hydrogen; $C_1$-$C_5$-alkoxy; halogen; or —$NR_5R_6$, wherein $R_5$ and $R_6$, independently from each other are hydrogen; $C_1$-$C_{12}$alkyl; —(CO)—H; or —(CO)—$C_1$-$C_5$alkyl; and An is an anion.

$C_1$-$C_{12}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl, 2-ethylhexyl, nonyl, decyl, undecy or dodecyl.

$C_1$-$C_5$alkoxy is preferably methoxy, ethoxy, propoxy, butoxy, pentyloxy, 3-pentyl, 2,2'-dimethylpropyloxy, cyclopentyloxy, cyclohexyloxy, n-hexyloxy, n-octyloxy, 1,1',3,3'-tetra-methylbutyloxy, 2-ethylhexyloxy, nonyloxy, decyloxy, undecyloxy or dodecyloxy.

Halogen is, for example, fluoride, chloride, bromide or iodide, especially chloride and fluoride. "Anion" denotes, for example, an organic or inorganic anion, such as halogen, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Preferably in formula (1)

An is selected from halide, sulfate, $C_1$-$C_8$alkyl sulfate, hydrogen sulfate, tosylate, mesylate, phosphate, boron tetrafluoride, carbonate, bicarbonate, lactate, formiate, acetate, propionate, triflate and a complex anion.

Most preferably the anion is

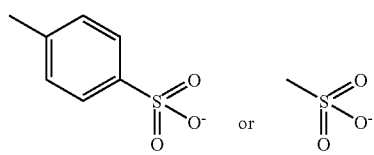

The following compounds are prefereably used in the present method:

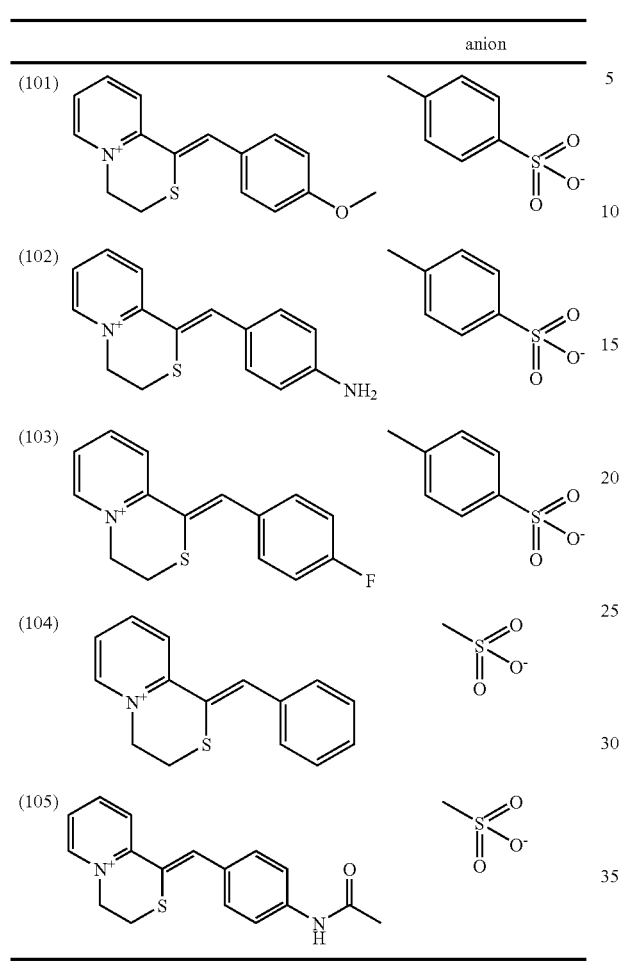

A further embodiment of the present invention relates to processes for the preparation of the compounds of formula (1).

Generally, the reaction is carried out according to the following reaction scheme:

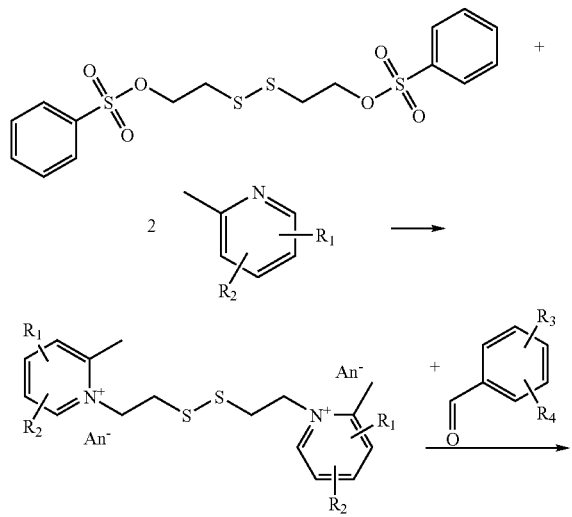

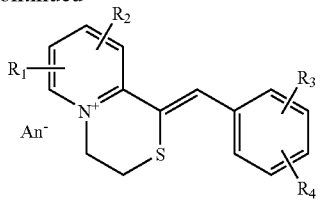

$R_1$, $R_2$, $R_3$ and $R_4$ and An are defined as in formula (1).

Customary, the temperature is in the range of 273 to 400 K, preferably is in the range of 290 to 360 K during the mixing of the starting compounds.

The reaction time is generally dependent on the reactivity of the starting compounds, on the reaction temperature chosen and on the desired conversion. The chosen duration of reaction is usually in the range from one hour to three days.

The selected reaction pressure is in the range from 70 kPa to 10 MPa, especially from 90 kPa to 5 MPa, and is more especially atmospheric pressure.

In addition, the reaction may be carried out with or without a solvent, but is preferably carried out in the presence of a solvent, preferably water, an organic solvents or solvent mixtures.

Organic solvents are for example, protic or aprotic polar organic solvents, such as alcohols, for example methanol, ethanol, n-propanol, isopropanol, butanol or glycols, especially isopropanol, or nitrile, such as acetonitrile or propionitrile, or amide, such as dimethyl-formamide, dimethylacetamide or N-methylpyridine, N-methylpyrolidon, or sulfoxide, such as dimethylsulfoxide, or mixtures thereof.

The reaction may be carried out in the presence of a catalyst.

The molar ratio of compound of formula (1a) to the catalyst is generally selected in the range from 10:1 to 1:5, especially in the range from 10:1 to 1:1.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or primary, secondary or tertiary amines, for example, such as chinuclidine, piperidine, N-methylpiperidine, pyridine, trimethylamine, ethylamine, diethylamine, triethylamine, trioctylamine, 1,4-diazabicyclo[2.2.2]octan, chinuclidine; or alkalimetal acetate, for example such as sodium acetate, potassium acetate, or lithium acetate.

Preferred are potassium acetate, sodium methoxide, piperidine, pyridine and 1,4-diazabicyclo[2.2.2]octan.

The product prepared according to the process of the present invention may be advantageously worked up and isolated, and if desired be purified.

Customary, the work up starts by decreasing the temperature of the reaction mixture in the range from 270 to 370 K, especially in the range from 290 to 300 K.

It may be advantageous to decrease the temperature slowly, over a period of several hours.

In general, the reaction product is usually filtered and then washed with water or a salt solution and subsequently dried.

Filtration is normally carried out in standard filtering equipment, for example Büchner funnels, filter presses, pressurised suction filters, preferably in vacuo.

The drying temperature is dependent on the pressure applied, usually at a temperature in the range from 313 to 363 K, especially from 323 to 353 K, and more especially in the range from 328 to 348 K. Drying is usually carried out in vacuo at 50-200 mbar.

The compounds of formula (1) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The stability, in particular the storage stability of the dyes according to the invention are excellent.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the compounds of formula (1) of the present invention may be combined with dyes of the same or other classes of dyes, especially with direct dyes, oxidation dyes (dye precursor/coupler) as well as a diazotized compound, or a capped diazotized compound; and/or cationic reactive dyes.

Direct dyes are of natural origin or may be prepared synthetically. They are uncharged, cationic or anionic, such as acid dyes.

The compounds of formula (1) may be used in combination with at least one single direct dye different from the compounds of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Körperpflegemittel e.V., Mannheim.

More preferred direct dyes which are useful for the combination with at least one single dye of formula (1), especially for semi permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo)pyridine, 2-nitro-5-glycerylmethylaniline, 3-methylamino-4-nitro-phenoxyethanol, 4-amino-2-nitrodiphenyleneamine-2'-carboxilic acid, 6-nitro-1,2,3,4,-tetrahydroquinoxaline, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the compounds of formula (1) may be combined with at least one cationic azo dye, for example the compounds as disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6 (compound of formula 106); or the cationic dye of formula (3) as described in EP-A-714,954, or with a yellow cationic dye of formula

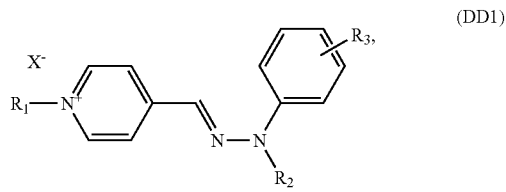

(DD1)

wherein
$R_1$ and $R_2$ are each independently of the other a $C_1$-$C_8$alkyl; or an unsubstituted or substituted benzyl;
$R_3$ is hydrogen; $C_1$-$C_8$alkyl; $C_1$-$C_8$alkoxy; cyanide; or halide; preferably hydrogen; and
$X^-$ is an anion; and preferably a compound of formula (DD1), wherein
$R_1$ is methyl; $R_2$ is benzyl; $R_3$ is hydrogen; and $X^-$ is an anion; or wherein
$R_1$ is benzyl; $R_2$ is benzyl; $R_3$ is hydrogen; and $X^-$ is an anion; or wherein
$R_1$ is benzyl; $R_2$ is methyl; $R_3$ is hydrogen; and $X^-$ is an anion.

Furthermore, cationic nitroaniline and anthraquinone dyes are useful for a combination with a compound of formula (1), for example the dyes as described in the following patent specifications: U.S. Pat. No. 5,298,029, especially in col 2, I. 33 to col 5, I. 38; U.S. Pat. No. 5,360,930, especially in col 2, I. 38 to col 5, I. 49; U.S. Pat. No. 5,169,403, especially in col 2, I. 30 to col 5, I. 38; U.S. Pat. No. 5,256,823, especially in col 4, I. 23 to col 5, I. 15; U.S. Pat. No. 5,135,543, especially in col 4, I. 24 to col 5, I 16; EP-A-818 193, especially on p. 2, I. 40 to p. 3, I. 26; U.S. Pat. No. 5,486,629, especially in col 2, I 34 to col 5, I. 29; and EP-A-758 547, especially on p. 7, I. 48 to p. 8, I. 19.

The compounds of formula (1) may also be combined with acid dyes, for example the dyes which are known from the international names (Color index), or trade names.

Preferred acid dyes which are useful for the combination with a dye of formula (1) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The compounds of formula (1) according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The compounds of formula (1) may also be combined with uncharged dyes, for example selected from the group of the nitroanilines, nitrophenylenediamines, nitroaminophenols, anthraquinones, indophenols, phenazines, phenothiazines, bispyrazolons, or bispyrazol aza derivatives and methines.

Furthermore, the compounds of formula (1) may preferably be used in combination with dye compositions containing oxidation dye precursors ("oxidation bases") and couplers.

Suitable oxidation dye systems are described for example in

DE 19 959 479, especially in col 2, I. 6 to col 3, I. 11;

"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes).

Preferred dye precursors are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, I. 50 to I 66 and on p. 3 I 8 to I 12, or cationic developer compounds as described in WO 00/43367, especially on p., 2 I 27 to p. 8, I. 24, in particular on p. 9, I. 22 to p. 11, I. 6.

Furthermore, dye precursors in their physiological compatible acid addition salt form, such as hydrochloride or sulfate can be used. Dye precursors, which have aromatic OH radicals are also suitable in their salt form together with a base, such as alkali metalphenolates.

More preferred dye precursors are p-phenylendiamine, p-toluoylendiamine, p-, m- o-amino-phenol, N,N-bis-(2-hydroxyethyl)-p-phenylenediamine sulfate, 2-amino-4-hydroxyethylamino-anisol sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H— pyrazol, 4-amino-m-cresol, 6-amino-m-cresol, 5-amino-6-chloro-cresol, 2,4,5,6-tetra-aminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, I. 33 to p. 3, I. 11.

Further preferred for a combination with a compound of formula (1) are the following oxidation dye precursors/coupler combinations:

the developer/-coupler combination 2,4,5,6-tetraminopyrimidine and 2-methylresorcine for assessing of red shades;

p-toluenediamine and 4-amino-2-hydroxytoluene for assessing of blue-violet shades;

p-toluenediamine and 2-amino-4-hydroxyethylaminoanisole for assessing of blue shades;

p-toluenediamine and 2,4-diamino-phenoxyethanol for assessing of blue shades;

methyl-4-aminophenol and 4-amino-2-hydroxytoluene for assessing of orange shades;

p-toluenediamine and resorcine for assessing of brown-green shades;

p-toluenediamine and 1-naphthol for assessing of blue-violet shades, or p-toluenediamine and 2-methylresorcine for assessing of brown-gold shades.

The compounds of formula (1) may also be used together with unsaturated aldehydes as disclosed in DE 19 717 224 (p. 2, I. 50 to I. 66 and on p. 3 I. 8 to I. 12) which may be used as direct dyes or, alternatively together with oxidation dye precursors.

Furthermore, autooxidizable compounds may be used in combination with the compounds of formula (1).

Autooxidizable compounds are aromatic compounds with more than two substituents in the aomatic ring, which have a very low redox potential and will therefore be oxidized when exposed to the air. The dyeings obtained with these compounds are very stable and resistant to shampoo.

Autooxidizable compounds are for example benzene, indol, or indoline, especially 5,6-dihydroxyindol or 5,6-dihydroxyindoline derivatives as described in WO 99/20234, especially on p. 26, I. 10 to p. 28, I. 15, or in WO 00/28957 on p. 2, third §.

Preferred autooxidizable benzene derivatives are 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxybenzene, and the salts of these compounds, which are accessible with acid.

Preferred autooxidizable indol derivatives are 5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroixyindol, 5,6-diacetoxyindol, acid of 5,6-dihydroxyindol-2-carbonacid, and the salts of these compounds, which are accessible with acid.

The compounds of formula (1) may also be used in combination with naturally occurring dyes, such as henna red, henna neutral, henna black, camomile blossom, sandalwood, black tea, Rhamnus frangula bark, sage, campeche wood, madder root, catechu, sedre and alkanet root. Such dyeings are described, for example, in EP-A-404 868, especially on p. 3, I. 55 to p. 4, I. 9.

Furthermore, the compounds of formula (1) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference.

Further preferred dyes or dye combinations which are useful for the combination with a compound of formula (1) according to the present invention are described in (DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;

(DC-02): U.S. Pat. No. 6,843,256, wherein cationic dyes are disclosed, especially the compounds of formulae (1), (2), (3) and (4) (col. 1, l. 27-col. 3, l. 20, and preferably the compounds as prepared in the examples 1 to 4 (col. 10, l. 42 to col. 13, l. 37; formulations col. 13, l. 38 to col. 15, l. 8;

(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein direct dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22-p. 4, l. 15) and anionic UV-absorbers (p. 4, l. 27-30) are disclosed; formulations p. 7, l. 50-p. 9, l. 56;

(DC-07): EP 998,908, wherein oxidation dyeings comprising a cationic direct dye and pyrazolo-[1,5-a]-pyrimidines (p. 2, l. 48-p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of Arianors and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, l. 3-12 and l. 30 to p. 14, and p. 28, l. 35-p. 30, l. 20; preferably p. 30, l. 25-p. 32, l. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, l. 40-col. 7, l. 14), optionally dispersed in an organic pulverulent excipient and/or a mineral pulverulent excipient, and a composition (C) containing one or more oxidizing agents are disclosed; formulations col. 8, l. 60-col. 9, l. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, l. 17-col. 13, l. 65; dyeing formulations in col. 2, l. 16 to col. 25, l. 55, a multi-compartment dyeing device is described in col. 26, l. 13-24;

(DC-13): WO 99/20235, wherein compositions of at least one cationic dye and at least one nitrated benzene dye with cationic direct dyes and nitro benzene direct dyes are described; on p. 2, l. 1 top. 7, l. 9, and p. 39, l. 1 to p. 40 l. 11, preferably p. 8, l. 12 to p.

25 l. 6, p. 26, l. 7 top. 30, l. 15; p. 1, l. 25 top. 8, l. 5, p. 30, l. 17 to p. 34 I 25, p. 8, l. 12 to p. 25 l. 6, p. 35, l. 21 to 27, especially on p. 36, l. 1 to p. 37;

(DC-14): WO 99/20234, wherein compositions comprising at least one direct cationic dye and at least one autooxidisable dye, especially benzene, indol and indoline derivatives are described, preferably direct dyes on p. 2, l. 19 to p. 26, l. 4, and autooxidisable dyes as disclosed especially on p. 26, l. 10 to p. 28, l. 15; dyeing formulations especially on p. 34, l. 5 to p. 35, Ii 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, l. 41 to p. 7, l. 52, dyeing formulations p. 19, l. 50-p. 22, l. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, l. 50 to p. 8, l. 44 are disclosed; dyeing formulations p. 21, l. 30-p. 22, l. 57;

(DC-17): WO 99/48856, wherein oxidation dyeing compositions comprising cationic couplers are disclosed, especially p. 9, l. 16-p. 13, l. 8, and p. 11, l. 20-p. 12, l. 13; dyeing formulations p. 36, l. 7-p. 39, l. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptids, aromatic hydroxy compounds, and/or at least one CH-active compound are disclosed p. 3, l. 42-p. 5 l. 25; dyeing formulations p. 8, l. 25-p. 9, l. 61.

In the dye combinations disclosed in the references (DC-01-DC-18) above, the compounds of formula (1) according to the present invention may be added to the dye combinations or dyeing formulations or may be replaced with at least one compound of formula (1).

The present invention also relates to formulations, which are used for the dyeing of organic materials, preferably keratin-containing fibers, and most preferably human hair, comprising at least (a) 0.001 to 5, preferably 0.005 to 4, more particularly 0.2 to 3% b.w. of at least one dye of formula (1);

(b) 1 to 40, preferably 5 to 30% b.w. of a solvent; and (c) 0.01 to 20% b.w. of an adjuvant.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, a gel, or an emulsion.

Customary the dyeing compositions are applied to the keratin-containing fiber in an amount of 50 to 100 g.

The dyeing compositions of the present invention are applied on the hair in a temperature range of 25 to 200, preferably 18 to 80, and most preferably from 20 to 40° C.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

One preferred embodiment of the present invention relates to the formulation of dyes, wherein the compounds of formula (1) are in powder form.

Powder formulations are preferably used if stability and/or solubility problems as for example described in DE 197 13 698, p. 2, I. 26 to 54 and p. 3, I. 51 to p. 4, I. 25, and p. 4, I. 41 to p. 5 I. 59, occur.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in customary amounts, for example emulsifiers may be present in the dyeing compositions in concentrations from 0.5 to 30% b.w. and thickeners in concentrations of from 0.1 to 25% b.w. of the total dyeing composition.

Further carriers for dying compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

A shampoo has, for example, the following composition:
0.01 to 5% b.w. of the compound of formula (1);
8% b.w of disodium PEG-5 laurylcitrate Sulfosuccinate, Sodium Laureth Sulfate;
20% b.w. of sodium cocoamphoacetate;
0.5% b.w. of methoxy PEG/PPG-7/3 aminopropyl dimethicone;
0.3% b.w. of hydroxypropyl guar hydroxypropytrimonium chloride;
2.5% b.w. of PEG-200 hydrogenated glyceryl pal mate; PEG-7 glyceryl cocoate;
0.5% b.w. of PEG-150 distearate;
2.2. % b.w of citric acid;
perfume, preservatives; and
water ad 100%.

The compounds of formula (1) may be stored in a liquid to paste-like preparation (aqueous or non-aqueous) or in the form of a dry powder.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:

non-ionic polymers, for example vinylpyrrolidone/vinyl acrylate copolymers, polyvinyl-pyrrolidone and vinylpyrrolidone/vinyl acetate copolymers and polysiloxanes;

cationic polymers, such as quaternised cellulose ethers, polysiloxanes having quaternary groups, dimethyldiallylammonium chloride polymers, copolymers of dimethyldiallyl-ammonium chloride and acrylic acid, as available commercially under the name Merquat® 280 and the use thereof in hair dyeing as described, for example, in DE-A-4 421 031, especially p. 2, I. 20 to 49, or EP-A-953 334;

acrylamide/dimethyldiallylammonium chloride copolymers, diethyl-sulfate-quaternised dimethylaminoethyl methacrylate/vinylpyrrolidone copolymers, vinylpyrrolidone/-imidazolinium methochloride copolymers;

quaternised polyvinyl alcohol:

zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;

anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;

thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;

structuring agents, such as glucose and maleic acid;

hair-conditioning compounds, such as phospholipids, for example soya lecithin, egg lecithin, cephalins, silicone oils, and conditioning compounds, such as those described in DE-A-19 729 080, especially p. 2, I. 20 to 49, EP-A-834 303, especially p. 2, I. 18-p. 3, I 2, or EP-A-312 343, especially p. 2, I. 59-p. 3, I. 11;

protein hydrolysates, especially elastin, collagen, keratin, milk protein, soya protein and wheat protein hydrolysates, condensation products thereof with fatty acids and also quaternised protein hydrolysates;

perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, substances for adjusting the pH value;

panthenol, pantothenic acid, allantoin, pyrrolidonecarboxylic acids and salts thereof, plant extracts and vitamins;

cholesterol;

light stabilisers and UV absorbers as listed in Table below:

TABLE 1

UV absorbers which may be used in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |

TABLE 1-continued

UV absorbers which may be used in the dyeing compositions of the present invention

| No. | Chemical Name | CAS No. |
|---|---|---|
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

- cationic benzotriazole UV absorbers as for example described in WO 01/36396 especially on p. 1, I. 20 to p. 2, I. 24, and preferred on p. 3 to 5, and on p. 26 to 37;
- cationic benzotriazole UV in combination with antioxidants as described in WO 01/36396, especially on p. 11, I. 14 to p. 18;
- UV absorbers in combination with antioxidants as described in U.S. Pat. No. 5,922,310, especially in col 2, I. 1 to 3;
- UV absorbers in combination with antioxidants as described in U.S. Pat. No. 4,786,493, especially in col 1, 42 to col 2, I. 7, and preferred in col 3, 43 to col 5, I. 20;
- combination of UV absorbers as described in U.S. Pat. No. 5,830,441, especially in col 4, I. 53 to 56;
- combination of UV absorbers as described in WO 01/36396, especially on p. 11, I. 9 to 13; or
- triazine derivatives as described in WO 98/22447, especially on p. 1, I. 23 to p. 2, I. 4, and preferred on p. 2, I. 11 to p. 3, I. 15 and most preferred on p. 6 to 7, and 12 to 16.

Suitable cosmetic preparations may usually contain from 0.05 to 40% b.w., preferably from 0.1 to 20% b.w., based on the total weight of the composition, of one or more

- UV absorbers;
- consistency regulators, such as sugar esters, polyol esters or polyol alkyl ethers;
- fats and waxes, such as spermaceti, beeswax, montan wax, paraffins, fatty alcohols and fatty acid esters;
- fatty alkanolamides;
- polyethylene glycols and polypropylene glycols having a molecular weight of from 150 to 50 000, for example such as those described in EP-A-801 942, especially p. 3, I. 44 to 55,
- complexing agents, such as EDTA, NTA and phosphonic acids,
- swelling and penetration substances, such as polyols and polyol ethers, as listed extensively, for example, in EP-A-962 219, especially p. 27, I. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;
- opacifiers, such as latex;
- pearlising agents, such as ethylene glycol mono- and distearate;
- propellants, such as propane-butane mixtures, $N_2O$, dimethyl ether, $CO_2$ and air;
- antioxidants; preferably the phenolic antioxidants and hindered nitroxyl compounds disclosed in ip.com (IPCOM # 000033153D);
- sugar-containing polymers, as described in EP-A-970 687;
- quaternary ammonium salts, as described in WO 00/10517;
- Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% b.w., based on the solids content of the preparations;

The dyeing compositions according to the present invention generally comprise at least one surfactant selected from zwitterionic or ampholytic, or more preferably anionic, nonionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

- linear fatty acids having 10 to 22 carbon atoms (soaps),
- ether carboxylic acids of formula $R—O—(CH_2—CH_2—O)_x—CH_2—COOH$, in which R is a linear alkyl group having 10 to 22 carbon atoms and x=0 or from 1 to 16,
- acyl sarcosides having 10 to 18 carbon atoms in the acyl group,
- acyl taurides having 10 to 18 carbon atoms in the acyl group,
- acyl isothionates having 10 to 18 carbon atoms in the acyl group,
- sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups,
- linear alkane sulfonates having 12 to 18 carbon atoms,
- linear $\alpha$-olefin sulfonates having 12 to 18 carbon atoms,
- $\alpha$-sulfo fatty acid methyl esters of fatty acids having 12 to 18 carbon atoms,
- alkyl sulfates and alkyl polyglycol ether sulfates of formula $R'—O(CH_2—CH_2—O)_x—SO_3H$, in which R' is a preferably linear alkyl group having 10 to 18 carbon atoms and x'=0 or from 1 to 12,
- mixtures of surface-active hydroxysulfonates according to DE-A-3 725 030;
- sulfated hydroxyalkylpolyethylene and/or hydroxyalkylenepropylene glycol ethers according to DE-A-3 723 354, especially p. 4, I. 42 to 62,
- sulfonates of unsaturated fatty acids having 12 to 24 carbon atoms and 1 to 6 double bonds according to DE-A-3 926 344, especially p. 2, I. 36 to 54,
- esters of tartaric acid and citric acid with alcohols which are addition products of approximately from 2 to 15 molecules of ethylene oxide and/or propylene oxide with fatty alcohols having from 8 to 22 carbon atoms, or
- anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$-carboxylic acids, such as oleic acid, stearic acid, isostearic acid and palmitic acid.

Surface-active compounds that carry at least one quaternary ammonium group and at least one —COO⁻ or —SO₃⁻ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazoline having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —SO₃H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a polyalkylene glycol ether group or a combination of polyol and polyglycol ether groups. Such compounds are, for example:

- addition products of 2 to 30 mol of ethylene oxide and/or 0 to 5 mol of propylene oxide with linearar fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyidimethyl-lammonium chloride, lauryidimethylammonium chloride, lauryidimethylbenzylammonium chloride and tricetyl-methylammonium chloride. Further cationic surfactants that can be used in accordance with the invention are quaternised protein hydrolysates.

Also suitable are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, I. 9 to p. 55, I. 2.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

A further preferred embodiment of the present invention relates to a method of treating keratin-containing fibers with heterocyclic compounds of formula (1).

In addition, the present invention relates to a method of
(a) treating the keratin-containing fibers with a compound of formula (1),
(b) wearing the coloured hair for the desired period of time,
(c) removing the colour applied in step (a) from hair by contacting the hair with an aqueous based colour removal composition.

A further preferred embodiment of the present invention therefore relates to a method of dyeing hair with an oxidative dye system, which comprises
(a) mixing at least one compound of formula (1) and optionally at least one dye precursor and at least one developer compound, and an oxidizing agent, which optionally contains at least one further dye, and
(b) contacting the keratin-containing fibers with the mixture as prepared in step a.

The pH-value of the oxidizing agent free composition is usually from 3 to 11, and in particular from 5 to 10, and most particular about 9 to 10.

Furthermore, the present invention relates to a process for dyeing keratin-containing fibers which comprises applying to that fiber a dye composition in an amount sufficient to dye said fiber, wherein said dye composition comprises
(a) at least one compound of formula (1); and
(b) at least one basifying agent in an amount sufficient to adjust the pH of said composition to 8.5 to 11, while simultaneously applying to that fiber at least one oxidizing agent whereby said oxidizing agent is mixed with said dye composition.

In general, the composition is left on the fiber for 0 to 60 minutes, in particular for 30 to 45 minutes at 15 to 45° C., usually in amounts of 30 to 120 g.

The oxidation dyeing process usually involves lightening, that is to say that it involves applying to the keratin-containing fibers, at basic pH, a mixture of bases and an oxidizing agent, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidizing agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

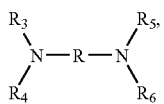

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

Generally the hair is rinsed after treatment with the dyeing solution and/or permanent-wave solution.

If the compounds of formula (1) are used together with an oxidizing dye, the oxidation dye systems together with the compounds of formula (1) are applied on the keratineous fiber in a ready-to-use composition, which comprises, on the one hand, a composition (A) comprising, in a medium which is suitable for dyeing, at least one developer compound, especially selected from para-phenylenediamines and bis(phenyl) alkylenediamines, and the acid-addition salts thereof, at least one coupler, especially selected from metaphenylenediamines and the acid-addition salts thereof, and at least one compound of formula (1), on the other hand, a composition (B) containing, in a medium which is suitable for dyeing, at least one oxidizing agent.

The compositions (A) and (B) are mixed together immediately before applying this mixture to the keratin-containing fibers.

Alternatively, the ready-to-use-composition comprises a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one compound of formula (1), and, finally, a composition (B) containing, in a medium which is suitable for dyeing, at least one oxidizing agent as defined above.

The compositions (A), (A') and (B) are mixed together immediately before applying this mixture to the keratin-containing fibers.

The composition (A') used according to this second embodiment may optionally be in powder form, the compound(s) of formula (1) (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

A very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

The pH value of the ready-to-use dyeing compositions is usually from 2 to 11, preferably from 5 to 10.

Another preferred method of applying formulations comprising the compounds of formula (1) on the keratin-containing fiber, preferably the hair is by using a multi-compartment dyeing device or "kit" or any other multi-compartment packaging system, as described for example in WO 97/20545 on p. 4, I. 19 to I 27.

The first compartment contains for example at least one compound of formula (1) and optionally further direct dyes and a basifying agent, and in the second compartment an oxidizing agent; or in the first compartment at least one compound of formula (1) and optionally further direct dyes, in the second compartment a basifiying agent and in the third compartment an oxidizing agent.

The compounds of formula (1) are suitable for all-over dyeing of the hair, that is to say when dyeing the hair on a first occasion, and also for re-dyeing subsequently, or dyeing of locks or parts of the hair.

The compounds of formula (1) are applied on the hair for example by massage with the hand, a comb, a brush, or a bottle, which is combined with a comb or a nozzle.

In the processes for dyeing according to the invention, whether or not dyeing is to be carried out in the presence of a further dye will depend upon the color shade to be obtained. Furthermore, the present invention relates to a process for dyeing keratin-containing fibers with the compounds of formula (1) and capped diazotised compounds, which comprises, a. treating the keratin-containing fibers under alkaline conditions with at least one capped diazotised compound and a coupler compound, and optionally a developer compound and optionally an oxidizing agent, and optionally in the presence of a further dye, and optionally with at least one compound of formula (1); and b. adjusting the pH in the range of 6 to 2 by treatment with an acid, optionally in the presence of a further dye, and optionally at least one compound of formula (1), with the proviso that at least in one step a. or b. at least one compound of formula (1) is present.

The capped diazotised compound and coupler compound and optionally the oxidizing agent and developer compound can be applied in any desired order successively, or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

Furthermore, the present invention relates to a process for dyeing keratin-containing fibers with the compounds of formula (1) and at least one acid dye.

The following Examples serve to illustrate the processes for dyeing without limiting the processes thereto. Unless specified otherwise, parts and percentages relate to weight. The amounts of dye specified are relative to the material being coloured. T, s, d, q and J, wherein t is a triplett, s is singulett, d is duplett, q is a quartett, and J is a coupling constant, define the NMR spectra values.

EXAMPLES A

Preparation of New Compounds

Example 1

Preparation of the Compound of Formula

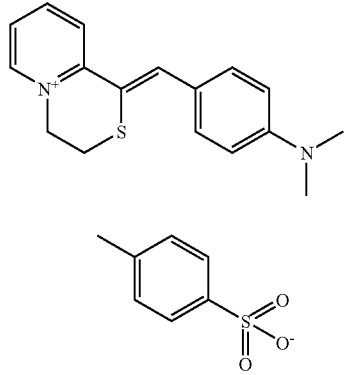

(101)

a. Alkylating Agent

A mixture of 15.4 g of 2,2-dithiodiethanol in 100 ml chloroform and 24.1 g pyridine are cooled with stirring to 0° C.

41.0 g of tosyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent and dissolved in two equivalent amounts of 2-methyl-pyridine. The temperature is raised to 60° C. and maintained at 60° C. during the following 24 hours.

c. Condensation 50 ml of dimethyl-formamide are added to the reaction mixture obtained in step b. The equivalent amount of dimethylamino-benzaldehyde and a catalytical amount of piperidine are added and the reaction mixture is stirred for 40 hours at 80° C. The reaction product is precipitated by cooling, separated by filtration and dried in vacuum to obtain 39 g of an orange solid product.

The product is recrystallized twice from isopropanol.

The product is characterized by the following data:

The HPLC-MS gives a main component of a monocation of the mass 283.

1H-NMR data in deuterated chloroform (128 scans)/360 MHz:

| Compound (101 | 9.62 | d | 6.8 | 1.00 | Py |
|---|---|---|---|---|---|
| | 828 | t | 6.7 | 0.98 | Py |
| | 7.92 | d | 6.7 | 1.02 | Py |
| | 7.81 | t | 6.6 | 1.03 | Py |
| | 7.701 | d | 7.0 | 1.97 | tosilate |
| | 7.58 | d | 6.1 | 1.967 | Phe |
| | 7.180 | s | | 1.025 | vinyl |
| | 7.11 | d | 6.9 | 1.846 | tosilate |
| | 6.71 | d | 6.4 | 2.05 | Phe |
| | 5.10 | m | | 2.00 | ethylene |
| | 3.56 | m | | 2.05 | ethylene |
| | 3.04 | s | | 6.08 | Dimethyl(amine) |
| | 2.326 | s | | 2.97 | Me-tosylate |

Example 2

Preparation of the Compound of Formula

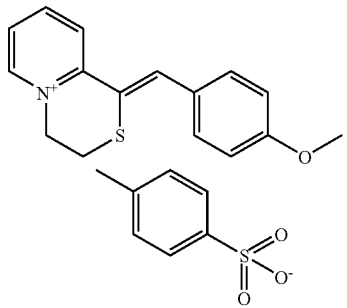

(102)

a. Alkylating Agent

A mixture of 15.4 g of 2,2-dithiodiethanol in 100 ml chloroform and 24.1 g pyridine are cooled with stirring to 0° C. and then 41.0 g of tosyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in the step b.

b. Alkylation

The alkylation agent obtained in step a. is delivered from the solvent and dissolved in two equivalent amounts of 2-methyl-pyridine.

The temperature is raised to 60° C. and maintained during the following 24 hours.

c. Condensation 50 ml of isopropanol are added to the reaction mixture obtained in step b.

The equivalent amount of anisaldehyde and a catalytical amount of anhydrous sodium acetate are added and the reaction mixture is stirred for 40 hours at 80° C.

The reaction product is precipitated by cooling, separated by filtration and dried in vacuum to obtain 29 g of a yellowish solid product.

The product is recrystallized twice from isopropanol.

The product is characterized by the following data:
The HPLC-MS gives a main component of a monocation of the mass 270.
1H-NMR data in deuterated methanol128 scans)/360 MHz:

| Compound (102) | 8.828 | d | 6.8 | 1.00 | Py |
|---|---|---|---|---|---|
| | 8.557 | t | 6.7 | 0.98 | Py |
| | 8.400 | d | 6.7 | 1.02 | Py |
| | 8.319 | t | 6.6 | 1.03 | Py |
| | 7.861 | d | 6.9 | 2.0 | Phe |
| | 7.705 | d | 7.0 | 1.97 | tosylate |
| | 7.50 | s | | 1.025 | vinyl |
| | 7.243 | d | 6.9 | 1.846 | tosilate |
| | 7.085 | d | 6.4 | 2.05 | Phe |
| | 4.86 | m | | 2.00 | ethylene |
| | 3.904 | s | | 3.00 | methyl |
| | 3.53 | m | | 2.05 | ethylene |
| | 2.36 | s | | 5.90 | tosylate |

Example 3

Preparation of the Compound of Formula

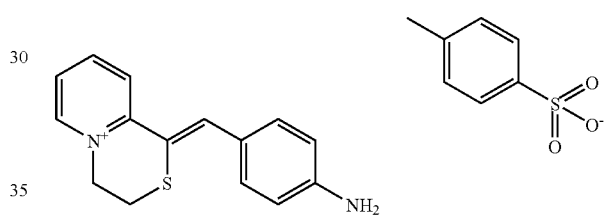

(103)

a. Alkylating Agent

A mixture of 15.4 g of 2,2-dithiodiethanol in 100 ml ethylene and 24.1 g pyridine are cooled with stirring to 0° C. and then 41.0 g of tosyl chloride are added in small amounts maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent and dissolved in two equivalent amounts of 2-methyl-pyridine.

The temperature is raised to 70° C. and maintained during the following 24 hours.

c. Condensation 50 ml of tolurnr are added to the reaction mixture obtained in step b.

The equivalent amounts of amino-benzaldehyde and a catalytical amount of piperidine are added and the reaction mixture is stirred for 30 hours at 80° C.

The reaction product is precipitated by cooling, separated by filtration and dried in vacuum to obtain 41 g of an orange solid product.

The product is recrystallized twice from isopropanol.

The product is characterized by the following data:
The HPLC-MS gives a main component of a monocation of the mass 255.
1H-NMR data in deuterated chloroform (128 scans)/360 MHz.

| Compound (103) | 8.708 | d | 6.8 | 0.98 | Py |
| --- | --- | --- | --- | --- | --- |
| | 8.461 | t | 6.7 | 1.00 | Py |
| | 8.257 | d | 6.7 | 1.00 | Py |
| | 7.833 | t | 6.6 | 1.03 | Py |
| | 7.711 | d | 6.9 | 2.0 | Phe |
| | 7.705 | d | 7.0 | 1.97 | tosylate |
| | 7.445 | s | | 1.025 | vinyl |
| | 7.219 | d | 6.9 | 1.846 | tosylate |
| | 6.814 | d | 6.4 | 2.05 | Phe |
| | 4.828 | m | | 2.00 | ethylene |
| | 3.53 | m | | 2.05 | ethylene |
| | 2.36 | s | | 6.10 | tosylate |

The product is characterized by the following data:
The HPLC-MS gives a main component of a monocation of the mass 258.
1H-NMR data in deuterated methanol (128 scans)/360 MHz:

| Compound (104) | 8.904 | d | 6.8 | 1.00 | Py |
| --- | --- | --- | --- | --- | --- |
| | 8.608 | t | 6.7 | 0.98 | Py |
| | 8.360 | d | 6.7 | 1.02 | Py |
| | 7.96 | t | 6.6 | 1.03 | Py |
| | 7.781 | t | 8 | 2.0 | Phe |
| | 7.718 | d | 7.0 | 1.97 | tosylate |
| | 7.548 | s | | 1.025 | vinyl |
| | 7.317 | t | 8 | 1.967 | Phe |
| | 7.11 | d | 6.9 | 2.046 | tosilate |
| | 4.911 | m | | 2.00 | ethylene |
| | 3.557 | m | | 2.05 | ethylene |
| | 2.363 | s | | 2.98 | tosilate |

Example 4

Preparation of the Compound of Formula

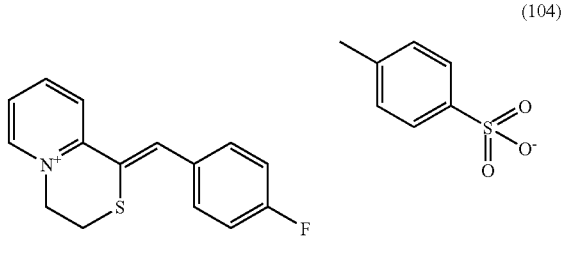

(104)

Example 5

Preparation of the Compound of Formula

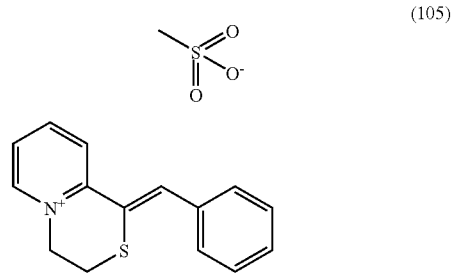

(105)

a. Alkylating Agent

A mixture of 15.4 g of 2,2-dithiodiethanol in 100 ml chloroform and 24.1 g pyridine are cooled with stirring to 0° C.
41.0 g of tosyl chloride are added in small amounts maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent dissolved in two equivalent amounts of 2-methyl-pyridine.

The temperature is raised to 60° C. and maintained during the following 24 hours.

c. Condensation 50 ml of isopropanol are added to the reaction mixture obtained in step b.

The equivalent amounts of 4-fluoro-benzaldehyde and a catalytical amount of piperidine are added and the reaction mixture is stirred for 30 hours at 70° C.

The reaction product is precipitated by cooling, separated by filtration and dried in vacuum to obtain 35 g of a yellow solid product.

The product is recrystallized from isopropanol.

a. Alkylating Agent

A mixture of 15.4 g of 2,2-dithiodiethanol in 100 ml chloroform and 24.1 g pyridine are cooled with stirring to 0° C. and then 31.0 g of mesyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of methanesulfonate diester is used as starting compound in the step b.

b. Alkylation

The alkylation agent obtained in step a. is freed from the solvent and dissolved in two equivalent amounts of 2-methyl-pyridine.

The temperature is raised to 60° C. and maintained during the following 24 hours.

c. Condensation 50 ml of dimethyl-formamide are added to the reaction mixture obtained in step b.

The equivalent amount of benzaldehyde and a catalytical amount of piperidine are added and the reaction mixture is stirred for 40 hours at 80° C.

The reaction product is precipitated by cooling, separated by filtration and dried in vacuum to obtain 33 g of a yellow solid product.

The product is recrystallized twice from isopropanol.

The product is characterized by the following data:
The HPLC-MS gave a main component of a monocation of the mass 240.
1H-NMR data in deuterated Methanole (128 scans)/360 MHz:

| Compound (105) | 8.802 | d | 6.8 | 0.98 | Py |
| | 8.521 | t | 6.7 | 1.00 | Py |
| | 8.30 | d | 6.7 | 1.00 | Py |
| | 7.910 | t | 6.6 | 1.03 | Py |
| | 7.751 | d | 6.9 | 2.02 | Phe |
| | 7.705 | d | 7.0 | 1.97 | tosilate |
| | 7.495 | s | | 1.02 | vinyl |
| | 7.219 | d | 6.9 | 1.86 | tosilate |
| | 7.03 | t | 6.4 | 2.05 | Phe |
| | 6.814 | t | 6.5 | 1.02 | Phe |
| | 4.878 | m | | 2.00 | ethylene |
| | 3.54 | m | | 2.05 | ethylene |
| | 2.363 | s | | 2.90 | tosilate |

Example 6

Preparation of the Compound of Formula (106)

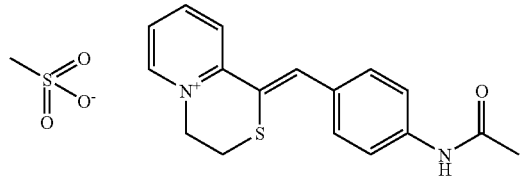

a. Alkylating Agent

A mixture of 15.4 g of 2,2-dithiodiethanol in 100 ml chloroform and 24.1 g pyridine are cooled with stirring to 0° C. and then 31.0 g of mesyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of methanesulfonate diester is used as starting compound in step b.

b. Alkylation

The alkylation agent obtained in step b. is delivered from the solvent dissolved in two equivalent amounts of 2-methylpyridine. The temperature is raised to 60° C. and maintained during the following 24 hours.

c. Condensation 50 ml of dimethyl-formamide are added to the reaction mixture obtained in step b.

The equivalent amount of acetylamino-benzaldehyde and a catalytical amount of piperidine are added and the reaction mixture is stirred for 40 hours at 80° C.

The reaction product is precipitated by cooling, separated by filtration and dried in vacuum to obtain 44 g of a brown solid product.

The product is recrystallized twice from isopropanol.

The product is characterized by the following data:
The HPLC-MS gave a main component of a monocation of the mass 297.
1H-NMR data in deuterated methanol (128 scans)/360 MHz:

| Compound (106) | 8.718 | d | 6.8 | 0.99 | Py |
| | 8.561 | t | 6.7 | 1.00 | Py |
| | 8.357 | d | 6.7 | 1.00 | Py |
| | 7.883 | t | 6.6 | 1.03 | Py |
| | 7.761 | d | 6.9 | 2.03 | Phe |
| | 7.495 | s | | 1.02 | vinyl |
| | 6.914 | d | 6.4 | 2.05 | Phe |
| | 4.848 | m | | 2.02 | ethylene |
| | 3.53 | m | | 2.05 | ethylene |
| | 2.724 | s | | 2.90 | mesilate |
| | 2.140 | s | | 3.12 | acetyl |

B. APPLICATION EXAMPLES

The washing fastness of the dyed hair is analyzed by the Grey scale according to Industrial organic pigments by Herbst&Hunger, 2nd ed. engl. S. 61) Nr 10: DIN 54 001-8-1982, "Herstellung und Bewertung der Aenderung der Farbe", ISO 105-A02-1993.

In the following application examples compositions within the below given definitions are used:

Example B1

0.1% of the compound of formula (101) is dissolved in a 10% solution of a non-ionic surfactant (Plantacare 200UP, Henkel) adjusted to pH 9.5 using citric acid or monoethanolamine. This dyeing solution is applied on the dry hair (two blond, two middle blond and two damaged hair strands) at room temperature and allowed to stand for 20 min. at room temperature. Then, the strands are rinsed under tap water (Water temperature: 37° C.+/−1° C.; flow rate of water: 5-6 l/min.) and dried for 12 hours.

Washing fastness: 10× washed with shampoo.

Results:

| Strand | Colour result | Washing fastness | Light fastness |
|---|---|---|---|
| blond | Orange/good | 3 | 4-5 |
| middelblond | Orange/good | 1-2 | 5 |
| damaged | Orange/good | 1-2 | 5 |

Example B2

A dye emulsion, containing 1% of the compound of formula (101); pH=9.8

| Cetylstearylalcohol | 11.00 |
|---|---|
| Oleth-5 | 5.0 |
| Oleic acid | 2.5 |
| Stearic acid monoethanolamide | 2.5 |
| Coco fatty acid monoethanolamide | 2.5 |
| Sodium laurylsulphate | 1.7 |
| 1,2-Propanediol | 1.0 |
| Ammoniumchloride | 0.5 |
| EDTA, Tetrasodiumsalt | 0.2 |
| Perfume | 0.4 |

-continued

| | |
|---|---|
| Cornproteinhydrolysate | 0.2 |
| Silica | 0.1 |
| Ammonia 25% | 0.1 |
| Water | Ad 100 | is mixed with the same weight of 6% hydrogen peroxide solution and the mixture is immediately applied to a tress of brown hair at room temperature.

After 30 minutes the tress is rinsed (Water temperature: 37° C.+/−1° C.; flow rate of water: 5-6 l/min.), shampooed, rinsed and dried.

The tress has been dyed to an intensive copper shade.

Example B3

A dye emulsion, containing
0.1% of the compound of formula (101)
3.5% Cetearyl alcohol
1.0% Ceteareth 30
0.5% Glycol Distearate
3.0% Stearamide DEA
1.0% Sodium Oleoamphohydroxypropyl Sulfonate
0.5% Polyquarternium-6 and
water ad 100% is applied for 30 minutes, at room temperature, to bleached human hair, and rinsed (Water temperature: 37° C.+/−1° C.; flow rate of water: 5-6 l/min.).

The result is a very attractive vibrant copper dyeing with good fastnesses.

Example B4

A dye emulsion containing

| | |
|---|---|
| Cetearyl Alcohol | 12.000 |
| Ceteareth-25 | 5.000 |
| Glyceryl Stearate SE | 2.500 |
| Glycol Distearate | 0.500 |
| Polysorbate 60 | 0.500 |
| Oleth-10 | 2.000 |
| Cetearyl Octanoate | 0.750 |
| Deionized Water 70° C. | 72.400 |
| Disodium EDTA | 0.050 |
| Compound of formula (101) | 0.900 |
| Monoethanolamine 99% | 1.000 |
| Hydrolyzed Wheat Protein 20% | 1.000 |
| Monoethanolamine 99% | ~0.900 |
| Fragrance Drom 854 148 Linden Blossom | 0.500 |
| pH-Value: | 9.90-10.40 | is applied for 30 minutes, at room temperature, to middle blond human hair, and rinsed (Water temperature: 37° C.+/−1° C.; flow rate of water: 5-6 l/min.).

The result is a very attractive vibrant copper dyeing with good fastnesses.

Example B5

The dye emulsion of example B4 is mixed with the same weight of 6% hydrogen peroxide solution and the mixture is immediately applied to a tress of brown hair at room temperature. After 30 minutes the tress is rinsed (Water temperature: 37° C.+/−1° C.; flow rate of water: 5-6 l/min.), shampooed, rinsed and dried.

The tress has been dyed to an intensive copper shade.

Example B6

60 ml of part A, 60 ml of part B and 3 ml of part C are mixed in a mixing bowl or applicator bottle and the mixture is immediately applied to a tress of brown hair at room temperature. After 30 minutes the tress is rinsed (Water temperature: 37° C.+/−1° C.; flow rate of water: 5-6 l/min.), shampooed, rinsed and dried. The tress has been dyed an intensive copper.

Part A
Shade: Pure Red

| INGREDIENT | w/w % |
|---|---|
| Deionized Water RT | 20.00 |
| Sodium Sulfite | 0.60 |
| Disodium EDTA | 0.05 |
| Cocamidopropyl Betaine 30% | 4.00 |
| Propylene Glycol | 2.50 |
| Monoethanolamine 99% | 1.00 |
| Toluene-2,5-Diamine Sulfate | 0.25 |
| p-Aminophenol | 0.50 |
| 4-Amino-2-Hydroxytoluene | 0.70 |
| 2-Methyl-5-Hydroxyethylaminophenol | 0.50 |
| 2-Amino-4-Hydroxyethyl AA Sulfate | 0.10 |
| Erythorbic Acid | 0.40 |
| Deionized Water RT | 43.55 |
| Hydroxyethylcellulose - Natrosol 250 HHR CG | 0.75 |
| Deionized Water RT | 10.00 |
| Isopropyl Alcohol | 8.00 |
| Oleth-10 | 1.00 |
| Oleic Acid | 1.10 |
| Lactamide MEA | 1.00 |
| Fragrance Drom 837 375 Tropical Fever | 0.50 |
| Dihydroxypropyl PEG-5 Linoleammonium Chloride | 0.50 |
| Hydrolyzed Soy Protein | 0.50 |
| Monoethanolamine 99% | ~2.50 |
| Total: | 100.00 |

Part B
Developer 6%

| INGREDIENT | w/w % |
|---|---|
| Deionized Water RT | 80.50 |
| Disodium Phosphate | 0.15 |
| Salcare SC80 | 5.00 |
| Glycerin 99% | 1.00 |
| Sodium Laureth Sulfate 27% | 1.00 |
| Etidronic Acid 60% | ~0.35 |
| Hydrogen Peroxide 50% | 12.00 |
| Total: | 100.00 |

Part C

| INGREDIENT | w/w % |
|---|---|
| Deionized Water RT | 97.18 |
| Compound of formula (101) | 1.00 |
| Total: | 100.00 |

Example B7

A dye emulsion, containing 1% of the compound of formula (101); pH=10.5

| INGREDIENT | w/w % |
|---|---|
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Deionized Water 70° C. | 66.65 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Total: | 100.00 | is mixed with 1.5 weight of a 9% hydrogen peroxide solution and the mixture is immediately applied to a tress of brown hair (Water temperature: 37° C.+/−1° C.; flow rate of water: 5-6 l/min.). After 30 minutes the tress is rinsed (Water temperature: 37° C.+/−1° C.; flow rate of water: 5-6 l/min.), shampooed, rinsed and dried.

The tress has been dyed to an intensive copper shade.

Example B8

A dye emulsion, containing
1% of the dye of formula (101) and

| INGREDIENT | w/w % |
|---|---|
| Deionized Water RT | 64.68 |
| Acrylates/C10-30 Alkyl Acrylate Crosspolymer | 0.55 |
| Sodium Hydroxide 25% | 0.03 |
| DMDM Hydantoin | 0.50 |
| Sodium Cocoamphoacetate 32% | 15.00 |
| Ococamidopropyl Betaine 30% | 3.00 |
| Decyl Glucoside | 3.00 |
| Polyquaternium-7 | 0.50 |
| PEG-15 Copolyamine | 0.50 |
| PEG-75 Lanolin | 0.50 |
| Deionized Water RT | 10.00 |
| Disodium EDTA | 0.05 |
| Basic Orange 31 | 0.08 |
| Basic Yellow 87 | 0.01 |
| Basic Red 51 | 0.01 |
| PEG-40 Hydrogenated Castor Oil | 0.95 |
| Fragrance Drom 837 375 Tropical Fever | 0.45 |
| Citric Acid 25% Solution | ~0.20 |
| Total: | 100.00 | is applied for 30 minutes, at room temperature, to blond human hair, and rinsed (Water temperature: 37° C.+/−1° C.; flow rate of water: 5-6 l/min.).

The result is a very attractive vibrant copper dyeing with good fastnesses.

Example B9

A tress of blond hair is shampooed with a shampoo at room temperature, containing
0.1% of the compound of formula (101) and

| Disodium PEG-5 Laurylcitrate Sulfosuccinate, Sodium Laureth Sulfate | 8.25% |
|---|---|
| Sodium Cocoamphoacetate | 20.9% |
| Methoxy PEG/PPG-7/3 Aminopropyl Dimethicone | 0.5% |
| Hydroxypropyl Guar hydroxypropyltrimonium Chloride | 0.3% |
| PEG-200 Hydrogenated Glyceryl Palmate; PEG-7 Glyceryl Cocoate | 2.5% |
| PEG-150 Distearate | 0.5% |
| Citric Acid (30%) | 2.2% |
| Perfume; Preservatives | q.s. |
| Water | Ad 100% |

After 5 minutes the tress is rinsed (Water temperature: 37° C.+/−1° C.; flow rate of water: 5-6 l/min.) and dried.
The tress has been dyed to an intensive copper shade.

Example B10

A conditioner containing 0.1% of the compound of formula (101) and

| Cetyl Alcohol | 3.00% |
|---|---|
| Ceterareth-25 | 0.50% |
| Distearyldimonium Chloride | 1.00% |
| Quaternium-80 | 0.50% |
| Citric Acid | Ad pH = 5 |
| Perfumes; Preservatives | q.s. |
| Water | Ad 100% | is applied to a tress of shampooed blond hair at room temperature.

After 15 minutes the tress is rinsed (Water temperature: 37° C.+/−1° C.; flow rate of water: 5-6 l/min.) and dried.

The tress has been dyed to an intensive copper shade.

The invention claimed is:

1. Method of dyeing keratin-containing fibers comprising treating the fiber with at least one compound of formula (1)

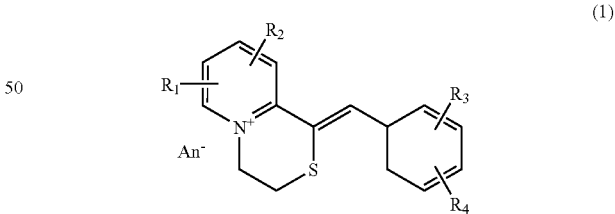

wherein
$R_1$, $R_2$, $R_3$, $R_4$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_5R_6$; —$NO_2$; —(CO)H or (CO)—$C_1$-$C_5$alkyl; or $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl;

$R_5$ and $R_6$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; or phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy; and An⁻ is an anion.

2. Method according to claim 1, wherein
$R_1$, $R_2$ and $R_3$ independently from each other are hydrogen; or $C_1$-$C_{12}$alkyl.

3. Method according to claim 1, wherein
$R_4$ is hydrogen; $C_1$-$C_5$-alkoxy; halogen; or —$NR_5R_6$, wherein
$R_5$ and $R_6$, independently from each other are hydrogen; $C_1$-$C_{12}$alkyl; —(CO)—H; or —(CO)—$C_1$-$C_5$alkyl.

4. Method according to claim 1, wherein
An⁻ is selected from halide, sulfate, $C_1$-$C_8$alkyl sulfate, hydrogen sulfate, tosylate, mesylate, phosphate, boron tetrafluoride, carbonate, bicarbonate, lactate, formiate, acetate, propionate, triflate and a complex anion.

5. Method according to claim 1, wherein the compounds of formula (1) are of formula (2)

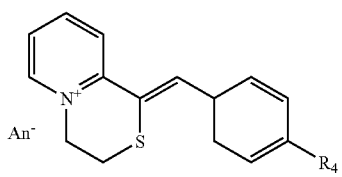

(2)

wherein
$R_4$ is hydrogen; $C_1$-$C_5$-alkoxy; halogen; or —$NR_5R_6$;
$R_5$ and $R_6$, independently from each other are hydrogen; $C_1$-$C_{12}$alkyl; —(CO)—H; or —(CO)—$C_1$-$C_5$alkyl; and
An⁻ is an anion.

6. A method according to claim 1, comprising
(a) dyeing the keratin-containing fiber with at least one single compound of formula (1)
(b) wearing the coloured hair for the desired period of time, and
(c) removing the colour applied in step (a) from hair by contacting the hair with an aqueous based colour removal composition.

7. A method according to claim 1, comprising applying to the fiber a dye composition in an amount sufficient to dye said fiber, wherein said dye composition comprises
(a) at least one compound of formula (1); and
(b) at least one basifying agent in an amount sufficient to adjust the pH of said composition to 8.5 to 11,
while simultaneously applying to the fiber at least one oxidizing agent whereby said oxidizing agent is mixed with said dye composition.

8. A hair dyeing composition comprising at least
(a) 0.001 to 5% b.w. of at least one dye of formula (1) according to claim 1;
(b) 1 to 40% b.w. of a solvent; and
(c) 0.01 to 20% b.w. of an adjuvant.

9. A composition according to claim 8 in form of a shampoo, conditioner, gel or emulsion.

10. A composition according to claim 8 comprising at least one single compound of formula (1), and a direct dye and/or an oxidation dye and/or a reactive dye.

11. Compounds of formula (1)

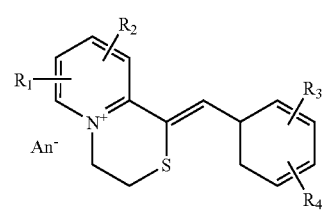

(1)

wherein
$R_1$, $R_2$, $R_3$, $R_4$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, —(CO)—H or —(CO)—$C_1$-$C_5$alkyl; —$NR_5R_6$; —$NO_2$; —(CO)—H; or —(CO)—$C_1$-$C_5$alkyl;
$R_5$ and $R_6$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; or phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1C_5$alkylamino, —$NO_2$, carboxy or hydroxy; and An⁻ is an anion.

12. A method for the preparation of the compounds of formula (1), according to the following reaction scheme:

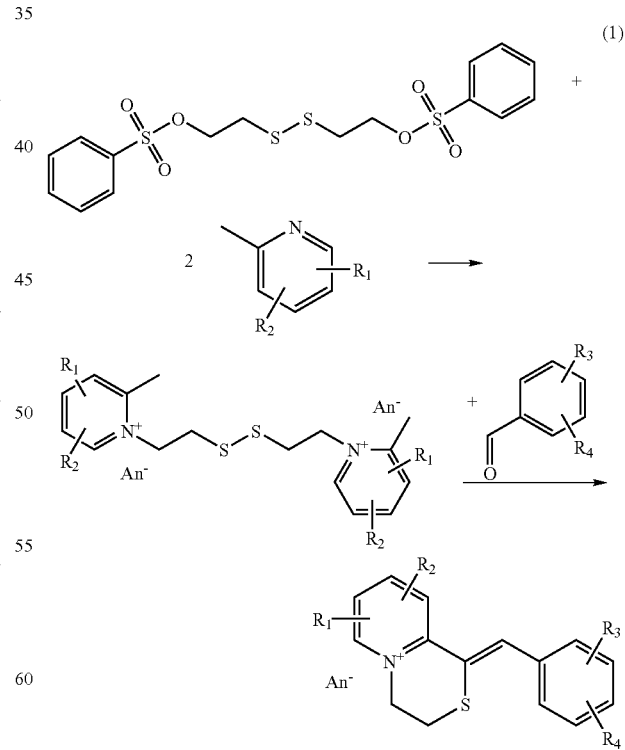

(1)

wherein
$R_1$, $R_2$, $R_3$, $R_4$ independently from each other are hydrogen; hydroxy; —S—H; —S—$C_1$-$C_{12}$alkyl; halogen;

$C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_5R_6$; —$NO_2$; —(CO)H or (CO)—$C_1$-$C_5$alkyl; or $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl;

$R_5$ and $R_6$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; or phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy; and $An^-$ is an anion.

* * * * *